US011355998B2

(12) United States Patent
Bauer et al.

(10) Patent No.: US 11,355,998 B2
(45) Date of Patent: Jun. 7, 2022

(54) METHOD AND EQUIPMENT FOR COOLING GENERATORS

(71) Applicant: SVOBATECH AG, Zug (CH)

(72) Inventors: Thomas Bauer, Zürich (CH); Matthias Svoboda, Würenlingen (CH)

( * ) Notice: Subject to any disclaimer, the term of this patent is extended or adjusted under 35 U.S.C. 154(b) by 0 days.

(21) Appl. No.: 17/299,066

(22) PCT Filed: Nov. 4, 2019

(86) PCT No.: PCT/EP2019/080078
§ 371 (c)(1),
(2) Date: Sep. 14, 2021

(87) PCT Pub. No.: WO2020/126185
PCT Pub. Date: Jun. 25, 2020

(65) Prior Publication Data
US 2022/0149699 A1 May 12, 2022

(30) Foreign Application Priority Data
Dec. 21, 2018 (CH) ..................................... 01581/18

(51) Int. Cl.
*H02K 9/10* (2006.01)
*H02K 9/24* (2006.01)
*G01M 3/28* (2006.01)

(52) U.S. Cl.
CPC ............ *H02K 9/10* (2013.01); *G01M 3/2815* (2013.01); *H02K 9/24* (2013.01)

(58) Field of Classification Search
CPC .................................. H02K 9/10; H02K 9/29
(Continued)

(56) References Cited

U.S. PATENT DOCUMENTS 6,459,750 B1 * 10/2002 Itoo .......................... H02K 9/19
376/402
7,730,713 B2 * 6/2010 Nakano ..................... F02C 7/10
60/39.83
(Continued)

FOREIGN PATENT DOCUMENTS

DE       102016106225 A1    10/2017
JP          H037040 A         1/1991
(Continued)

OTHER PUBLICATIONS

International Search Report of PCT/EP2019/080078 with English translation, dated Feb. 5, 2020.
(Continued)

*Primary Examiner* — Jose A Gonzalez Quinones
(74) *Attorney, Agent, or Firm* — CUSPA Technology Law Associates, P.A.; Yi Li

(57) ABSTRACT

According to the method, either CO2-free air or pure nitrogen N2 is pumped into the cooling circuit selectively depending on system parameters. To this end, the method ensures that the air injection rate is high enough that, under normal conditions, the hydrogen concentration in the tank and in the riser remains below 2% H2. On air injection, the oxygen O2 (>2 ppm) in the cooling water reacts with the copper in the cooling ducts and a layer of copper oxide forms on the inner walls of said ducts. No reaction is triggered by the injection of nitrogen N2. The CO2 content in the injection air and, at the same time, also the H2 content in the exhaust air are continuously measured and monitored, and an alarm is triggered if adjustable limit values are exceeded. The equipment for performing the method comprises an electronic control unit (65) with an input field and display as a control box, and a pump and a pipe circuit for drawing air in from the riser. The control unit (65) can evaluate all the measured data from the sensors and analy-
(Continued)

Figure 1:
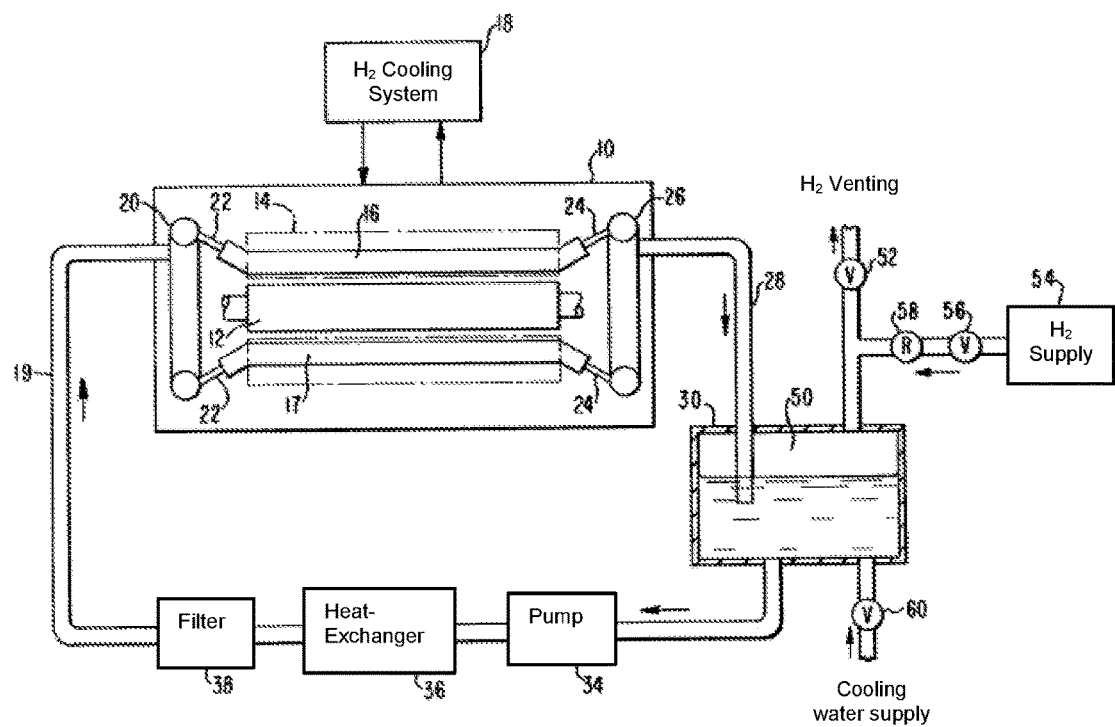

sers connected to the pipe and can at least check the CO2 content in the supply air and the H2 content in the riser (13) and display the hydrogen leakage.

6 Claims, 3 Drawing Sheets

(58) Field of Classification Search
USPC .......................................... 310/52, 54, 56, 59
See application file for complete search history.

(56) References Cited

U.S. PATENT DOCUMENTS

| | | | | |
|---|---|---|---|---|
| 8,564,237 | B2* | 10/2013 | Bandaru | H02K 5/124 |
| | | | | 310/59 |
| 2007/0277593 | A1* | 12/2007 | Salem | G01M 3/228 |
| | | | | 73/40.7 |
| 2009/0260518 | A1 | 10/2009 | Wright et al. | |

FOREIGN PATENT DOCUMENTS

| | | |
|---|---|---|
| JP | H05268750 A | 10/1993 |
| JP | H0844081 A | 2/1996 |
| KR | 101439523 B1 | 9/2014 |

OTHER PUBLICATIONS

Written Opinion of the International Search Authority of PCT/EP2019/080078 with English translation, dated Feb. 5, 2020.

International Preliminary Examination Report (IPER) of International Preliminary Examining Authority (IPEA) of PCT/EP2019/080078 with English translation, dated Mar. 16, 2021.

Notification of transmittal of translation of the International Preliminary Report on Patentability (PCT/IB/338) dated Jun. 24, 2021 containing an official English translation of International Preliminary Report on Patentability (Chapter II of PCT) of PCT/EP2019/080078 (Original IPRP dated Mar. 16, 2021).

* cited by examiner

METHOD AND EQUIPMENT FOR COOLING GENERATORS

This invention relates to a system for efficiently cooling the copper pipes of large electrical generators. The smallest and small generators are cooled with air, medium-sized ones with hydrogen, and with large generators, there is no avoiding of a water cooling. There are 1 m to 12 m long bars in the stator, which form the stator winding. These bars consist of bundles of up to 40 copper conductors. Hydrogenerators sometimes have hundreds of rods. Some of these copper conductors are hollow and form cooling channels with a cross section of a few square millimeters, through which water is pumped.

About 50% of all generators are operated with cooling water with an oxygen content of >2 ppm. The oxygen in the water reacts with the inner surfaces of these hollow copper conductors of large generators and a layer of copper oxide is formed on the walls of the cooling channels. This is a flowing process in that a new layer is continuously built up while a part of the layer is eroded by the flowing water. In the ideal case, the layer should remain in the same thickness over time, i.e. the layer structure and layer erosion should be in balance.

Large generators for power generation are often equipped with direct water cooling in the copper winding. The cooling water circulates in a closed circuit with continuous demineralization in a partial bypass flow. This guarantees ultrapure water conditions to minimize interactions with the system materials. In particular, the copper surfaces in the stator winding, which are directly exposed to the cooling water, must be kept as stable as possible. To do this, the water chemistry must be carefully controlled. In addition to soluble impurities, which are controlled by means of the ion exchanger in the demineralization bypass, the oxygen content must be kept either very low or very high. If the cooling is operated with a lot of $O_2$ in the cooling water, with more than 2 ppm, a stable CuO layer forms, while with a low $O_2$ content, below 20 ppb, attempts are made to minimize the formation of copper oxide. An unstable copper oxide mixture forms in a range of $O_2$ content in the cooling water between 20 ppb and 2 ppm. In particular, attempts are made to avoid an $O_2$ content between 200 ppb and 1000 ppb, because the CuO layer is the most unstable at this $O_2$ content. Rather, one tries, therefore, either to go towards 0 ppb with the $O_2$ content, or to drive with an $O_2$ content of over 2000 ppb. With a high $O_2$ content, a stable layer of mainly CuO forms on the inner walls of the cooling channels. Another aspect to be considered is the $CO_2$ content in the cooling water, because $CO_2$ lowers the pH value of the cooling water and this then attacks the CuO layer, i.e. this layer becomes soluble and unstable, which in the worst case leads to blockages of the cooling channels.

In order to control the oxygen content, gas can be injected into the system. For systems with a low oxygen content this would usually be nitrogen $N_2$, for systems with a high oxygen content it would usually be air. Usually, in cases of low oxygen content, no gas is blown in, but a protective gas is kept in the tank. If air is blown in with a high oxygen content, this has the disadvantage that $CO_2$ is also introduced into the system, which, as mentioned, acidifies the water and thus destabilizes the oxide layer on the copper surfaces. To minimize this, the $CO_2$ should be removed from the air blown in beforehand.

In addition to water cooling, large generators are also cooled with hydrogen gas, which circulates inside the generator housing. Hydrogen molecules inevitably diffuse through the Teflon hoses into the cooling water system of the stator. However, if there is a leak in the copper rods of the stator or the connections, larger amounts of hydrogen will flow into the cooling water because the hydrogen pressure inside the generator housing is intentionally kept higher than the cooling water pressure. If $H_2$ penetrates into the cooling water, this is far less dangerous than if, conversely, cooling water would get into the generator housing.

The cooling water system must have a mechanism for degassing the water. Often this task is solved with a tank in the main stream, which has a vent line to the atmosphere. This venting also allows the hydrogen to escape, which, as explained above, inevitably enters the system in small quantities.

In the practical version there is a storage tank filled with cooling water, and air is pumped into it from below. The equilibrium content of a dissolved gas in the water is based on its partial pressure in the gas space of the storage tank. In the following, only systems are considered that are operated with a high oxygen content in the cooling water. The cooling water is saturated with $CO_2$-free air to enrich it with $O_2$. A portion of the $O_2$ reacts with the copper on the inner walls of the cooling channels and forms a copper oxide layer on them. The water that leaves the generator also contains little hydrogen, which in turn gasses out in the tank according to its partial pressure. The exhaust air with a very small proportion of $H_2$ is discharged from the storage tank via a vent riser into the open air. The oxygen enrichment serves to maintain an oxygen content of >2000 ppb to keep the copper oxide layer as stable as possible.

According to conventional theory, the air injection rate is deliberately kept low, on <0.15 CFM=4.25 litres/min, because it is assumed that a hydrogen content in the air or the hydrogen concentration in this air content can then be measured more easily than in a large volume of air, in which the hydrogen would only take a very small fraction and supposedly difficult to detect.

The expensive measuring devices supplied and installed by the generator manufacturers for determining the content in the exhaust air are mostly ignored in practice and are largely left aside to their fate. There is still no device that regularly measures the $CO_2$ content in the air that is being injected, but it is simply assumed that $CO_2$ is effectively removed. However, $CO_2$ in the blown air attacks the copper oxide layer on the inner walls of the cooling duct, as mentioned, and it is therefore worthwhile to know the $CO_2$ content in the air precisely and to recognize if the $CO_2$ removal is incorrect.

In practice it is stated by the manufacturers of the generators that no $CO_2$ occurs in the air blown in. This is usually true when the generators are put into operation for the first time, but after a few years of operation this does not always apply and considerable $CO_2$ proportions can be measured in the incoming air flow. Because at that point in time existing guarantees may have expired, the power plant operator is confronted with the problem and is left alone with the cooling ducts clogging. This problem usually only manifests itself when the cooling function is unintentionally impaired and the temperatures rise or even exceed an impermissible limit value. The power plant operators want a remedy to get this problem under control once and for all.

In the prior art, particular reference should be made to US 2007/0277593 A1. This patent is an update of an older patent for the old stator leakage monitoring with the most important changes being the reduction of the air injection rate to <0.15 CFM (=4.25 litres/min), which leads to an increased accuracy of the monitoring system to around 0.2 CFD hydrogen leak rate. The greatest disadvantage, however, is that with this low level of air injection under normal operating conditions, explosive gas concentrations, i.e. a mixture of hydrogen and air, can occur in the tank and in the vent line open to the atmosphere. There are more than 1'000 generators with a high oxygen content in the cooling water, all of which should have correct $CO_2$-free air injection. Hundreds of systems are in operation, some for decades, and maintenance is often not carried out consistently enough.

The object of the present invention is therefore to specify a method and an installation for more efficient and safer cooling of large electrical generators. The air injection should overall also be more cost-effective and reliably monitorable, and the $CO_2$ concentration in the air introduced into the cooling water should be measurable at all times and should be kept below a certain limit value.

The solution to this problem is a process for cooling the copper lines of large electric generators, according to which, depending on the system parameters, either $CO_2$-free air or pure nitrogen $N_2$ is pumped into the cooling circuit.

The purpose of this method and this installation is to introduce the appropriate gas into the system on the one hand and to continuously measure and monitor the hydrogen leakage on the other. To do this, the following is done:

1. For systems with a high oxygen content, $CO_2$-free air is injected; for systems with a low oxygen content, nitrogen $N_2$ is injected.
2. The hydrogen concentration in the vent line is continuously measured and monitored via a monitoring system.
3. With an electronic control unit as a control box and a display, a hydrogen leak is detected based on the measured data of the air flow and the hydrogen concentration and the key data are displayed.
4. The $CO_2$ concentration of the injected air is measured by a monitoring system and displayed on the control unit.
5. Additional instruments can optionally be connected in order to measure and comply with further chemical parameters of the cooling water system.

The installation for carrying out the method, for connection to a stator cooling water system, has a stator cooling water tank with an outgoing line and riser tube, the outgoing line returning the cooling water through pumps, heat exchangers, a filter and then optionally leads through an ion exchanger into the stator cooling water tank or into the cooling channels of a stator winding in a generator, and is characterized by the fact that it includes an air injection system with a control system, with measuring instruments for measuring $CO_2$ in the supply air and $H_2$ in the exhaust air, as well as with a control unit with operating elements, whereby limit values can be entered for the $CO_2$ concentration as well as for the $H_2$ concentration, and if these limit values are exceeded, an alarm can be emitted or measures can be initiated automatically.

Such an installation is shown in the figures using a schematic representation. Their components and their function as well as the procedure carried out with them are described and explained in detail.

Figure 2:
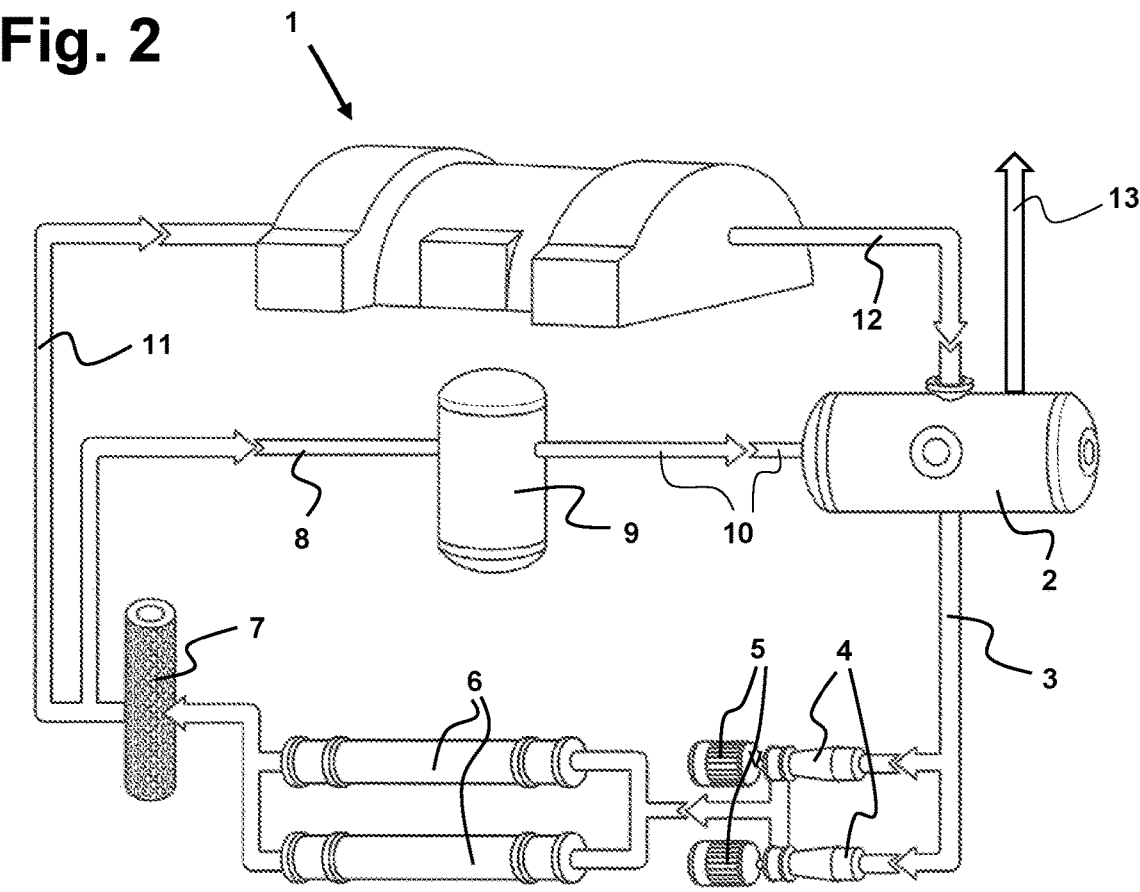
Figure 3:
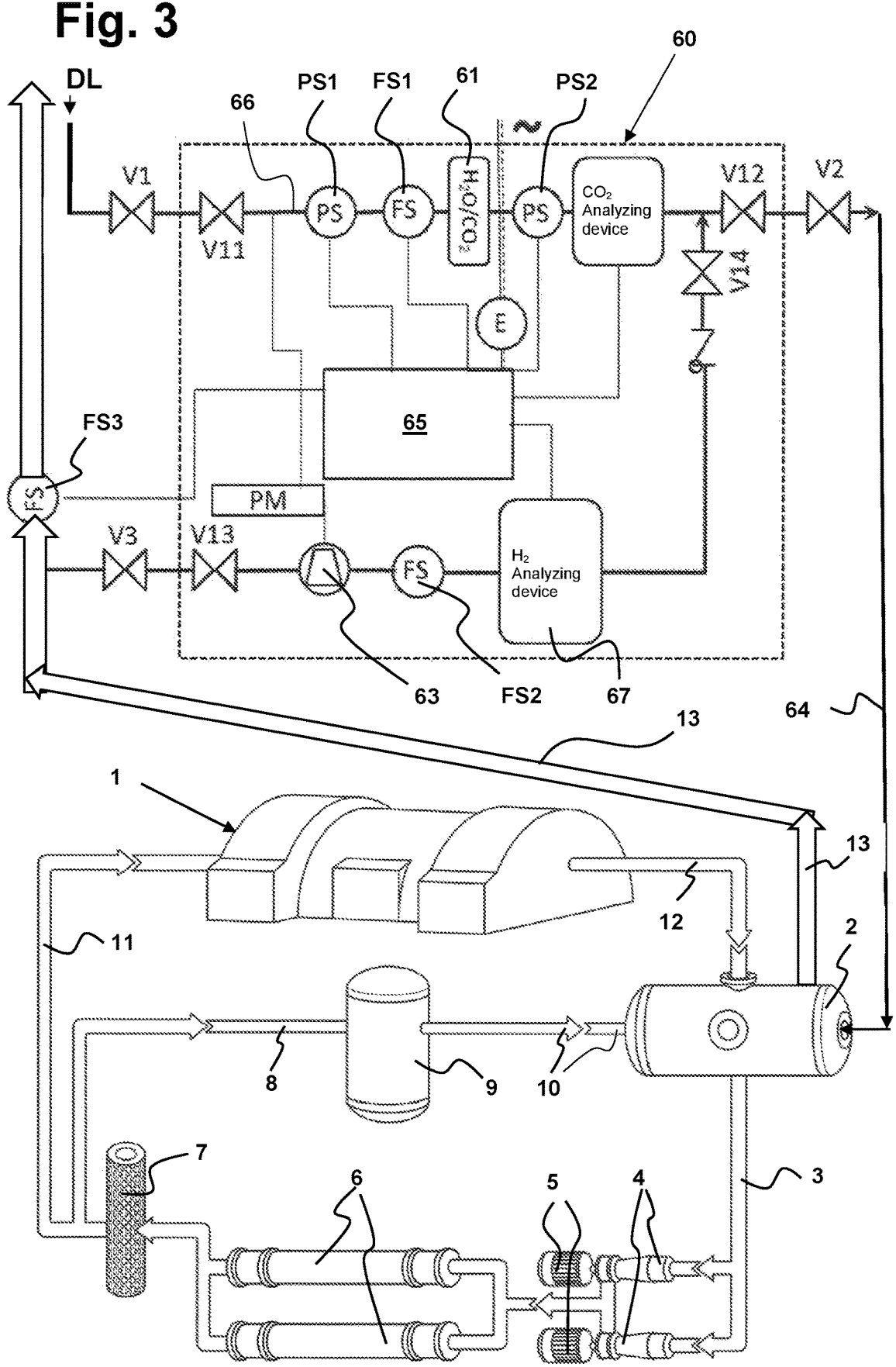
Figure 4:
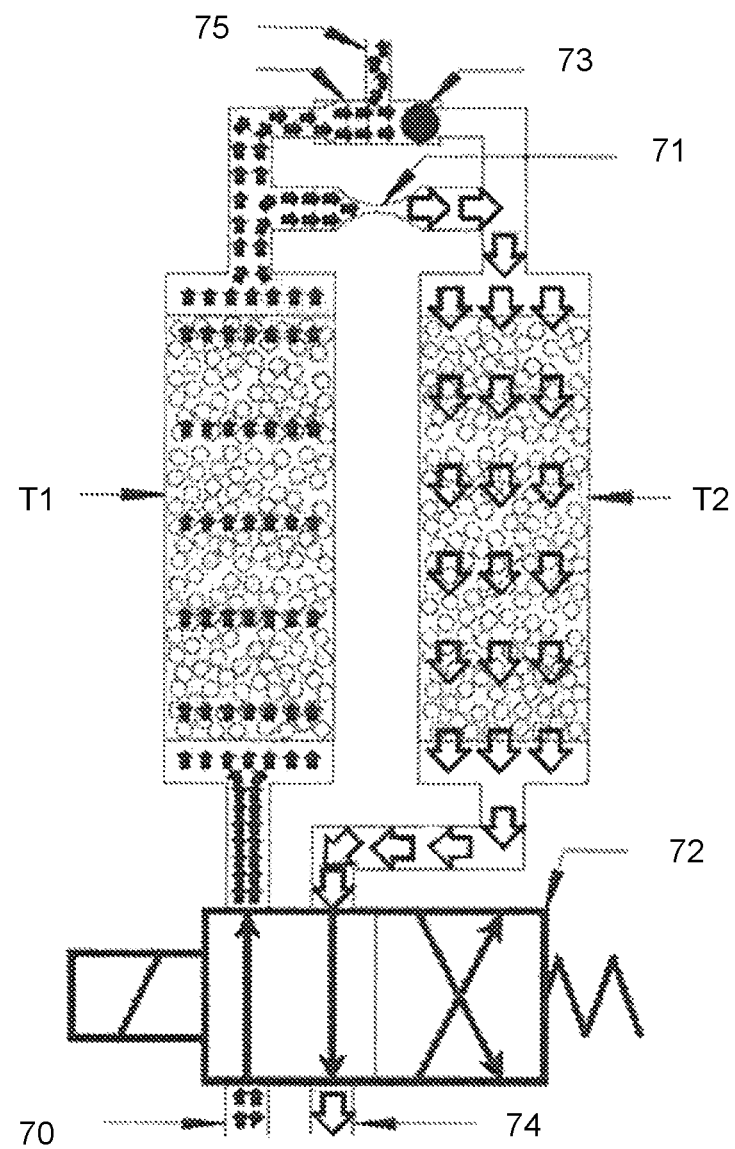

It shows:

FIG. 1: A schematic of a conventional generator cooling system with its components, in order to be able to show more clearly later the difference of the system according to the invention to it and the process operated with it;

FIG. 2: The scheme of a generator with copper rods with their the basic structure of the cooling circuit and the storage tank;

FIG. 3: The scheme of a generator with copper rods with their cooling circuit and the storage tank, the vent riser and the connected system according to the invention for carrying out the method;

FIG. 4: A diagram of a $CO_2$ separator for air.

First of all, the diagram according to FIG. 1 shows conventional cooling of a generator by means of water. In principle, it is about the cooling of the copper rods 16, 17 in FIG. 1. These copper rods are penetrated lengthwise by cooling channels. Lines made of Teflon are connected to these cooling channels 16, 17 as supply lines 22 and as discharge lines 24. There is a water tank 30, which is approx. ⅔ filled with water in the picture, while space 50 for gas or air is present above the water level. Cooling water can be fed to the tank via a valve 60. The cooling water flows down through the line 19 and then flows through a pump 34, a heat exchanger 36 and a filter 38, after which it is fed into the cooling channels 16, 17 via the distributor 20 and the supply lines 22 connected to it. After heat has been absorbed, it flows on the other side of the cooling channels via the discharge lines 24 and a collector 26 via the line 28 back into the tank 30. The generator or its copper rods are flushed with hydrogen gas $H_2$ from the outside. In the process, a small proportion of hydrogen $H_2$ inevitably diffuses through the Teflon hoses 22 and 24 into the interior of the cooling water. This hydrogen is then carried along by the cooling water and reaches the tank 30 and escapes from this via the riser. In addition, according to the state of the art, air is pumped into the cooling water. This proportion of air is deliberately kept low so that the volume flow remains below 4.25 litres/min. According to the common doctrine, only such a small proportion of air ensures that the hydrogen content in the cooling water can be reliably monitored.

FIG. 2 schematically shows a structure of a cooling system for a water-cooled generator 1. From a water tank 2, water is pumped via the line 3 through the pumps 4 and their associated electric motors 5 through a heat exchanger 6, in which heat is extracted from the water so that cool water then flows through a filter 7. After the filter 7, a water line 8 branches off into an ion exchanger 9, which water is then returned to the water tank 2 via the return line 10. This secondary flow is usually constant and serves to remove possible impurities, including $CO_2$, copper oxides, etc. Because the generator is flushed with hydrogen gas inside its housing, and a small proportion of hydrogen inevitably penetrates the cooling water through the Teflon hoses, this is fed back into the tank 2 together with the cooling water, which absorbed heat inside the generator. From there, the hydrogen escapes from the tank 2 via a long riser 13 into the atmosphere.

FIG. 3 shows the essential components of the installation according to the invention for carrying out the method, interconnected with a cooling system as just presented. A riser 13 leads upwards from the cooling water tank 2. Through this, hydrogen separated from the cooling water is released into the atmosphere. According to the new concept, an injection module is used which is encompassed by a dashed line in FIG. 3 and denoted overall by 60. The core of this concept is that $CO_2$-free air is supplied to the cooling circuit air, and this to a much greater extent than previously practiced, namely with an injection rate of more than 70 cm³/s. Up to now, this injection rate was chosen empirically and kept rather low. Compressed air DL, provided by the power plant, is pumped into the plant via a valve V1, which is present on the power plant side, via a further V11 belonging to the plant. With a pressure sensor PS1 for a range 0-100 psi, with a typical operating regime of 70 psi inlet and 50 psi outlet, the pressure of the sucked air is continuously measured, and the air flow rate is measured with a flow meter FS1 of 0-10 l/min.

The water and $CO_2$ content is separated in an aggregate 61. Another pressure sensor PS2 follows. Then the air flows through a $CO_2$ analyzing device. This one is able to display the $CO_2$ concentration from 0-1000 ppm. This $CO_2$ analyzing device 62 checks the cleaning effect of the $CO_2$ remover in order to guarantee $CO_2$-free air. The cooling air relieved of $CO_2$ then goes via the system-side valve V12 and then via a generator-side valve V2 via the line 64 to the cooling water tank 2. From this the cooling water enriched with $CO_2$-free air is finally pumped into the cooling channels in the copper rods of the generator 1. The injected air is not only used to enrich the cooling water with oxygen, but also some of the hydrogen $H_2$ is removed from the tank 2. This hydrogen-air mixture is drained off via the riser tube 13. Gas is withdrawn from the riser tube 13 and conveyed through the generator-side valve V3 and the system-side valve V13 via the pump wheel 63 and via a flow sensor FS2 to an $H_2$ analyzing device 67. The flow rate is kept lower here than in the air injection. The system can also be used for systems with a low oxygen content, in a simplified version even without $CO_2$ removal, by blowing in pure nitrogen $N_2$ instead of air.

As can also be seen from FIG. 3, electrical lines lead from all system components, namely from the pressure sensor PS1, from the flow meter FS1, from the unit 61 for the $H_2O/CO_2$ check, from the On/Off switch E, from the second pressure sensor PS2, from the $CO_2$-analyzing device 62, from the analyzing device 67, from the second flow meter FS2, from the pump PM for the flow of the cooling water and from the gas flow meter FS3 in the riser tube 13 to a central electronic control unit 65, which processes the data from all these components and transmits it to one associated display, whereby on this electronic control unit 65, desired parameters can be put in via an associated control panel for the control unit 65 as required, for example system-typical limit values. The illustrated valves V11 to V14 can optionally be electronically controllable solenoid valves in order to couple or uncouple the entire injection module 60 to or from a cooling system via the central electronic control unit 65, if necessary.

Newly, according to this cooling concept, air is pumped into the cooling water to a much greater extent, in order to achieve a volume flow of at least more than 5 litres/min. The volume flow of the air which has been cleaned of $CO_2$ and which is blown in is in fact sufficiently high in the context of a still acceptably large hydrogen leak to safely avoid an explosive mixture with hydrogen. If the leak is larger, the generator 1 has to be switched off for repairs anyway. This large volume flow of air differs from the common solutions that work with a volume flow of <4.25 litres/min. The sufficiently accurate detection of the $H_2$ content in the air for continuous monitoring is possible with new $H_2$ measuring devices which can even detect the smallest concentrations of $H_2$ in the air. This makes it possible to ensure that no explosive gas mixture is present in the cooling water tank 2 and the riser tube 13.

During several chemical cleanings on systems with a high oxygen content, one of the problems was the penetration of $CO_2$ into the stator cooling water system SCWS by the Stator-Leakage-Monitoring-System SLMS. The SLMS is equipped with a $CO_2$ remover, but in practice this often suffers from non-functioning or malfunction and provides incorrect feedback. Therefore, a really functioning $CO_2$-free air injection, preferably in combination with a really functioning hydrogen leakage monitoring system, is impressive, because the monitoring systems currently installed also often do not work satisfactorily.

As already mentioned, all data from the air inlet system and the $H_2$ analyzer 67 go to an electrical control unit 65 in a switch box. This creates a control box. In this at least the hydrogen leak rate is calculated and the most important parameters and alarms are displayed. The data storage can be set up on a permanent memory or USB stick as well as via a possible online data transfer to a server. The hydrogen leak rate can be calculated from the amount of air that is injected into the system and the concentration of hydrogen in the air that leaves the system using the following formula.

$$H2(\text{leakage}) = \frac{(-\text{Air (blown in)} * H2 \text{ (measured)})}{(H2 \text{ (measured)} - H2 \text{ (purity)})}$$

| | |
|---|---|
| $H_2$(leakage) | $H_2$ leakage rate |
| Air (blown) | air injection rate |
| ($H_2$ (measured) | measured concentration of $H_2$ |
| $H_2$ (purity) | $H_2$-purity of the cooling gas (typically 95-99%) |

What is special about this cooling concept is that it works with a deliberately higher air injection rate of >0.15 cfm or 70 cm³/s, and the risk of explosive gases in the ventilation line and the expansion tank is prevented, which is an essential safety feature. According to this new formula, the hydrogen purity of the hydrogen cooling gas is also included as a measured variable for calculating the amount of air injected.

The installation can have a modular structure to provide either just the air inlet system or just the hydrogen leakage monitoring. Depending on the version, the hydrogen leakage monitoring system must have an air inlet system. It always includes the switch box with an electronic control unit 65 as a control box, with all the necessary connections for future expansions if only one of the two modular systems is installed. Depending on the design of the cooling water system, there are up to 20 cubic feet or 0.5663 m³ $H_2$ leakages without causing an explosive mixture in the generator. These are medium-sized leaks that should or must obviously be repaired. For example, guide values and the indications to be implied from them are the following:

Dense system: 0.2 cubic feet=0.005663 m³/day: 0.08% $H_2$ in air

Normal system: 1 cubic feet=0.02832 m³/day: 0.38% $H_2$ in air 5 cubic feet=0.1416 m³/day: 1.91% $H_2$ in air: an acoustic and visual ALARM is given due to the presence of potentially explosive gas mixtures! From 4% a mixture is explosive and therefore dangerous. With an alarm threshold of 1.91% $H_2$ in the air, there is a safety margin of 100%.

Average leakage: 20 cubic feet=0.5663 m³/day: 7.63% $H_2$ in air

Severe leakage: >50 cubic feet=1,416 m³/day: >19.07% $H_2$ in air

The electronic control unit 65 belonging to the installation includes the following functions, which can be called up via a control panel and shown on the associated display.

Display of the air inlet flow

Alarm or display of the $CO_2$ concentration of the air injection

Display of the hydrogen concentration in the vent line

Calculation and display of the hydrogen leak rate

Data storage via USB
Potentially expandable for wireless data transmission to a server
Triggers an acoustic and visual alarm in the event of:
high $CO_2$ injection into the stator cooling water system SCWS
Malfunction of the air injection
Hydrogen content reaches >2%

In the future, the installation for this stator cooling water system (SCWS) can be combined with a chemical instrumentation module.

FIG. 4 shows a diagram of a $CO_2$ separator for air in order to explain its function. The air to be cleaned flows through the inlet 70 into the absorber column T1. The air, i.e. the air polluted with $CO_2$ and $H_2O$, then flows from bottom to top through this absorber column T1. Typically, more than 50% of the air purified in this absorber column T1 is used in the regeneration column T2 for its regeneration, while the remaining air is $CO_2$-free and can be drawn off via the check valve 71 and the connection 75 and is available for use. A solenoid four-way valve 72 is periodically changed from absorber column T1 to regeneration column T2 and vice versa. The regeneration can be assisted by a heater, for heating the regeneration column T2 or directly the regeneration gas by placing the column T2 under a negative pressure, and by releasing regeneration gas to ambient pressure, while the absorption in the column T1 is at an increased pressure level he follows.

The invention claimed is:

1. Installation for cooling cooling water-conducting copper pipes present in large electric generators cooled with hydrogen gas, by means of which installation a minimum quantity of $CO_2$-free air can be pumped into the cooling circuit in a targeted manner depending on the oxygen content of the cooling water in the case of a high oxygen content or pure nitrogen $N_2$ in the case of a low oxygen content, and whereby the critical air quantity ratio for the hydrogen $H_2$ contained in the cooling circuit can be kept outside the range of 4-75% $H_2$ in the air contained in the cooling water and thus outside the dangerous quantity ratio, with a connection to a stator cooling water system, wherein the system comprises a stator cooling water tank (2) with outgoing pipe (3) and riser tube (13), and wherein the outgoing pipe (3) leads the cooling water through pumps (4), heat exchangers (6), a filter (7) and thereafter optionally through an ion exchanger (9) back into the stator cooling water tank (2) or into the cooling channels of a stator winding in a generator (1), and wherein the installation includes an air injection system (60) with a control system with measuring instruments for the continuous measurement of $CO_2$ in the incoming supply air and $H_2$ in the outgoing exhaust air, and a control unit (65) with operating elements, wherein limit values can be entered for the $CO_2$ concentration and also for the $H_2$ concentration, above which an alarm can be output or measures can be initiated automatically, wherein the air injection system (60) is equipped with a plant-side valve (V11) via which oil- and dust-free air can be passed through the pipe (66) and then through a pressure sensor (PS1) and a flow meter (FS1), then through a $CO_2$ and $H_2O$ separation column (61) then via a second pressure sensor (PS2) into a $CO_2$ analyzer (62) and via a plant-side valve (V12) via a pipe (64) into the stator cooling water tank (2), and wherein from the riser tube (13) gas can be drawn off via a plant-side valve (V13) by means of a pump (PM) with a pump impeller (63), which can be fed via an H2 analyzer and a valve (14) into the pipe (66) and via the valve (V12) back via the pipe (64) into the stator cooling tank (2), and in that the control unit (65) is an electronic control unit (65) with an input field and display, which belongs to the plant as a control box and by means of which the measurement data of all connected sensors and analyzers of the system can be evaluated, at least the $CO_2$ content of the injected air and the $H_2$ content in the riser tube (13) can be measured, and by means of which an acoustic and optical alarm can be emitted when an adjustable limit value is exceeded.

2. Installation according to claim 1, characterized in that by means of the electronic control unit (65) an injection rate of air into the stator-cooling water system can be kept above 0.15 cfm, that the pressure sensors (PS1) and (PS2) have a measuring range of 0-100 psi, for measuring the pressure in the sucked-in air, and by means of the flow meter (FS) an air flow of 0.1-10 l/min can be measured.

3. Installation according to claim 1, characterized in that by means of the electronic control unit (65) and the $CO_2$ analyzer (62) the $CO_2$ content in the injected air can be measured and displayed in a measuring range of a $CO_2$ concentration of 1-1000 ppm, and at a freely selectable value an acoustic and optical alarm can be emitted.

4. Installation according to claim 1, characterized in that the installation can be used on stator cooling water systems with low oxygen content, without $CO_2$ removal, in that pure nitrogen $N_2$ can be blown into the stator cooling water system instead of air, and the hydrogen leakage can be measured and displayed.

5. Installation according to claim 1, characterized in that the electronic control unit (65) includes an app for sending acoustic alarms.

6. Installation according to claim 1, characterized in that by means of the electronic control unit (65) all data measured by the connected measuring devices can be read out via cable or wirelessly to one or more CPUs.

* * * * *